United States Patent
Sutton et al.

(10) Patent No.: US 11,718,598 B2
(45) Date of Patent: Aug. 8, 2023

(54) PROCESSES FOR THE PREPARATION OF ALKYL FURANS USING BIFUNCTIONAL COPPER CATALYSTS

(71) Applicant: TRIAD NATIONAL SECURITY, LLC, Los Alamos, NM (US)

(72) Inventors: Andrew Sutton, Los Alamos, NM (US); Xiaokun Yang, Santa Fe, NM (US); Cameron M. Moore, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 276 days.

(21) Appl. No.: 17/032,777

(22) Filed: Sep. 25, 2020

(65) Prior Publication Data

US 2021/0094926 A1    Apr. 1, 2021

Related U.S. Application Data

(60) Provisional application No. 62/906,262, filed on Sep. 26, 2019.

(51) Int. Cl.
*C07D 307/36* (2006.01)
*B01J 23/72* (2006.01)

(52) U.S. Cl.
CPC ............ *C07D 307/36* (2013.01); *B01J 23/72* (2013.01)

(58) Field of Classification Search
CPC ....... C07D 307/36; B01J 23/72; B01J 29/146; B01J 29/90; B01J 38/02; B01J 29/46; B01J 35/002; Y02P 20/584
USPC ...................................................... 549/506
See application file for complete search history.

(56) References Cited

U.S. PATENT DOCUMENTS

| 5,468,490 A | 11/1995 | Huber et al. |
| 5,627,288 A | 5/1997 | Fukawa et al. |
| 6,994,875 B2 | 2/2006 | Piccirilli et al. |
| 2014/0303114 A1 | 10/2014 | Mesina |

OTHER PUBLICATIONS

Koehle et al, Production of p-Methylstyrene and p-Divinylbenzene from Furanic Compounds, 2017, 10, 91-98. (Year: 2017).*
Wikipedia (Chemical Reactor, Nov. 2018, p. 1-6). (Year: 2018).*
Durst et al (Experimental Organic Chemistry, Properties of Common Solvent, 1980, p. 1460-147). (Year: 1980).*
Rodriguez-Sadna, Cesar et al., "Novel Antifeedant and Insecticidal Compounds from Avocado Indioblast Cell Oil," Journal of Chemical Ecology, 24(5):867-889, (1998).
Rodriguez-Saona, Cesar R. et al., "Alkylfurans: Effects of Alkyl Side-Chain Length on Insecticidal Activity," J. Nat. Prod., 62:191-193, (1999).
Wailzer, Bettina et al., "Structural Features for Furan-Derived Fruity and Meaty Aroma Impressions," Natural Product Communications, 11(10):1475-1479, (2016).
Weyerstahl, Peter et al., "Constituents of the Leaf Essential Oil of *Persea indica* (L.) K. Spreng.," Flavour and Fragrance Journal, 8:201-207, (1993).

* cited by examiner

*Primary Examiner* — Taylor V Oh
(74) *Attorney, Agent, or Firm* — Alston & Bird LLP

(57) ABSTRACT

The present disclosure relates to the selective hydrodeoxygenation (HDO) of bio-based furanic ketones with a bifunctional copper-based catalyst in the presence of a solvent to prepare alkyl furans with high yield, purity, and scalability. The alkyl furans prepared herein are useful in the preparation of surfactants.

16 Claims, 6 Drawing Sheets

¹H NMR (400 MHz, Chloroform-d)
δ 7.30 (dd, J = 1.8, 1.1 Hz, 1H), 6.28 (dd, J = 3.3, 1.8 Hz, 1H), 5.97 (dd, J = 3.3, 1.1 Hz, 1H), 2.62 (t, J = 7.6 Hz, 2H), 1.71 – 1.53 (m, 2H), 1.27 (brm, 18H), 0.89 (t, J = 6.8 Hz, 3H).

¹³C NMR (101 MHz, CDCl₃)
δ 156.65, 140.60, 110.01, 104.49, 31.94, 29.68, 29.66, 29.57, 29.39, 29.37, 29.21, 28.06, 28.00, 22.70, 14.12.

PROCESSES FOR THE PREPARATION OF ALKYL FURANS USING BIFUNCTIONAL COPPER CATALYSTS

CROSS-REFERENCE TO RELATED APPLICATIONS

This application claims the benefit of priority to U.S. Provisional Patent Application No. 62/906,262, filed on Sep. 26, 2019, the content of which is incorporated by reference herein in its entirety for all purposes.

GOVERNMENT INTEREST

The United States government has certain rights in this invention pursuant to Contract No. 89233218CNA000001 between the United States Department of Energy and TRIAD National Security, LLC for the operation of Los Alamos National Laboratory.

FIELD

The subject matter described herein relates to the selective hydrodeoxygenation (HDO) of furanic ketones to alkyl furans with a bi-functional copper-based catalyst.

BACKGROUND

Current cleaning products on the market contain builder ingredients to boost function, while maintaining product safety and shelf life. These petro-based builder chemicals increase product cost, volume, and biodegrade poorly. Surfactants, which could eliminate the need for these additional chemicals and generate eco-friendly cleaning products, are thus needed.

Oleo-Furan Surfactants (OFS), which are made from bio-based alkyl furans comprising natural oils with furan building blocks, exhibit excellent cleaning performance and can be used to replace both active cleaning ingredients and builders in commercial cleaning products. OFS can be used to make multi-functional and environmentally friendly cleaning materials, while reducing the overall energy consumption.

While alkyl furans have shown promise in OFS, the synthetic preparation of the alkyl furans, themselves, has proven to be a challenging endeavor, especially on the industrial scale. Problems related to selectivity, yield, and scalability have limited the use of the compounds in a number of different applications. Therefore, there is a need for improved preparations of alkyl furans. The subject matter described herein addresses this unmet need.

BRIEF SUMMARY

In certain aspects, the subject matter described herein is directed to a method for preparing a compound of Formula I,

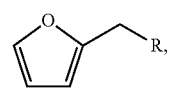

(I)

comprising contacting a compound of Formula II

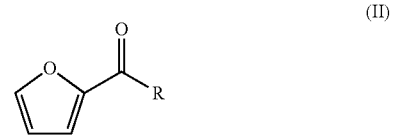

(II)

with a bifunctional copper-based catalyst for selective hydrodeoxygenation of the ketone moiety in the presence of a solvent, wherein R is alkyl.

These and other aspects are described fully herein.

DETAILED DESCRIPTION

Figure 1A:
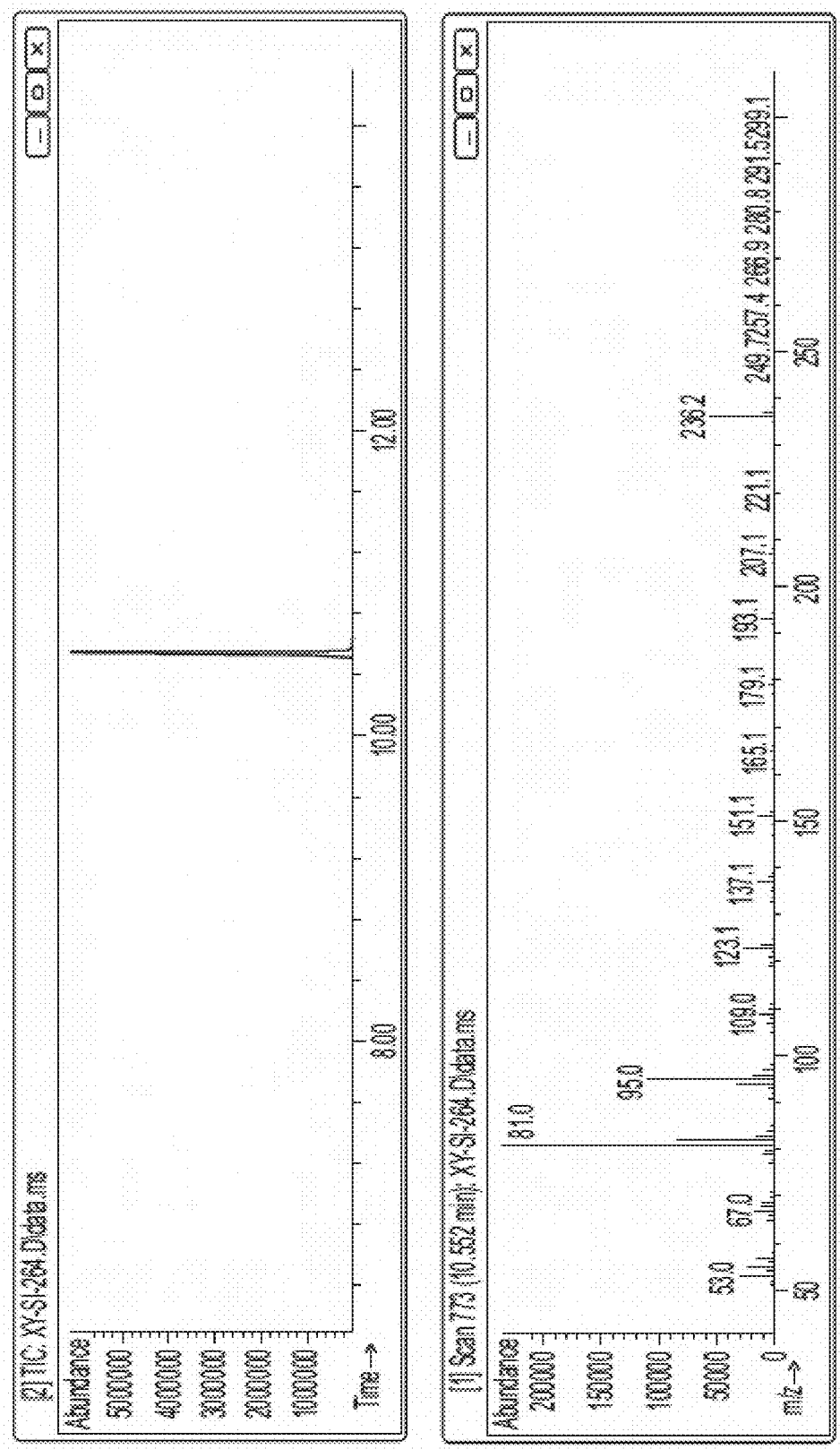
FIG. 1A shows GC-MS spectra of products from selective HDO of 2-dodecanoylfuran in a batch reaction. Reaction conditions: 0.1 g 2-dodecanoylfuran, 0.05 g 10% Cu/zeolite Y (Si/Al=2.55), 3 mL hexane, 220° C., $H_2$ atmosphere, 150 psi initial hydrogen pressure, 5 hours.

Disclosed herein are efficient methods for the selective hydrodeoxygenation of furanic ketones in the presence of a bifunctional copper-based catalyst to prepare alkyl furans with improved selectivity, yield, and scalability. The methods disclosed herein are safe and controllable, environmentally friendly, and utilize readily available reagents.

Copper chromite ($2CuO-Cr_2O_3$) is the catalyst generally employed in the preparation of alkyl furans from bio-based furanic ketones. However, copper chromite is a very fine powder, which makes it difficult to separate after reaction. When employed in catalytic reactions, Cr(III) in copper chromite has been shown to oxidize to its toxic hexavalent ion, Cr(VI). The observed leaching of Cr(VI) from chromite into the final product in these reactions is of great concern. The search for a more eco-friendly catalyst for converting furanic ketones to alkyl furans is therefore needed.

The present methods use bifunctional copper-based catalysts as a new class of heterogeneous catalysts for the selective hydrodeoxygenation of furanic ketones to alkyl furans. The methods disclosed herein successfully achieve hydrodeoxygenation of the ketone moiety of the furanic ketone while keeping the furan ring intact. The bifunctional copper-based catalysts demonstrate higher selectivity than copper chromite in the hydrodeoxygenation of the ketone moiety in furanic ketones. Additionally, the bifunctional copper-based catalysts do not suffer from toxic metal ion leaching, unlike in the case of Cr(VI) in copper chromite, and also employ more cost-effective materials. The preparation of alkyl furans in high selectivity with the bifunctional copper-based catalysts disclosed herein is achieved in both a batch reactor and a continuous flow system, demonstrating the scalability of the method. The catalysts additionally exhibit excellent regeneration in catalytic cycling experiments. As such, the bifunctional copper-based catalysts are therefore not only more environmentally friendly and economical than copper chromite, but also more effective catalysts on the industrial scale.

The as-synthesized alkyl furans can be used in a number of applications. With their hydrophobic furan and hydrophilic alkyl tail, the compounds may serve as surfactants, particularly as Oleo-Furan Surfactants. Surfactants are a key ingredient in cleaning products. As such, the bio-based OFS have the potential to create more environmentally friendly and cost effective cleaning materials. The efficient, eco-friendly methods for preparing alkyl furans disclosed herein can further the industrial preparation of OFS.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, "and/or" refers to and encompasses any and all possible combinations of one or more of the associated listed items, as well as the lack of combinations when interpreted in the alternative ("or").

The terms "approximately," "essentially," and "substantially" as used herein represent an amount close to the stated amount that still performs a desired function or achieves a desired result. For example, in some embodiments, as the context may dictate, the terms "approximately" and "substantially" may refer to an amount that is within less than or equal to 10% of the stated amount. The term "generally" as used herein represents a value, amount, or characteristic that predominantly includes or tends toward a particular value, amount, or characteristic.

As used herein, conditional language used herein, such as, among others, "can," "could," "might," "may," "e.g.," and the like, unless specifically stated otherwise or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

As used herein, "alkyl" refers to an unbranched or branched saturated hydrocarbon chain. As used herein, alkyl has 1 to 50 carbons (i.e., $C_{1-50}$ alkyl), 1 to 25 carbons (i.e., $C_{1-25}$ alkyl), 1 to 20 carbon atoms (i.e., $C_{1-20}$ alkyl), 1 to 12 carbons (i.e., $C_{1-12}$ alkyl), 1 to 11 carbons (i.e., $C_{1-11}$ alkyl), 1 to 8 carbon atoms (i.e., $C_{1-8}$ alkyl), 1 to 6 carbon atoms (i.e., $C_{1-6}$ alkyl), 1 to 5 carbon atoms (i.e., $C_{1-5}$ alkyl), or 3 to 5 carbon atoms (i.e., $C_{3-5}$ alkyl). Examples of alkyl groups include, e.g., methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl and 3-methylpentyl. When an alkyl residue having a specific number of carbons is named by chemical name or identified by molecular formula, all positional isomers having that number of carbons may be encompassed; thus, for example, "butyl" includes n-butyl (i.e., —$(CH_2)_3CH_3$), sec-butyl (i.e., —$CH(CH_3)$ $CH_2CH_3$), isobutyl (i.e., —$CH_2CH(CH_3)_2$) and tert-butyl (i.e., —$C(CH_3)_3$); and "propyl" includes n-propyl (i.e., —$(CH_2)_2CH_3$) and isopropyl (i.e., —$CH(CH_3)_2$). In certain embodiments, alkyl has 11 carbon atoms.

As used herein, "bifunctional catalyst" refers to a catalyst that can be used not only as an oxidative catalyst, but also as a reductive one. As used herein, "bifunctional copper-based catalyst" refers to a bifunctional catalyst comprising the transition metal copper.

As used herein, "HDO" refers to hydrodeoxygenation. As used herein, "hydrodeoxygenation" refers to the removal of oxygen by catalytic reaction with hydrogen.

As used herein, "ketone" refers to the functional group, $RC(=O)R'$ where R and R' can be a variety of carbon-containing substituents. As used herein, "ketone moiety" refers to the ketone portion of a molecule comprising its carbonyl group $C(=O)$.

As used herein, the term "contacting" refers to allowing two or more reagents to contact each other. The contact may or may not be facilitated by mixing, agitating, stirring, and the like.

As used herein, "selective hydrodeoxygenation of the ketone moiety" refers to exclusively hydrodeoxygenating the carbonyl group $C(=O)$ in a ketone to produce a saturated alkyl group.

As used herein, "heterogeneous catalyst" refers to a catalyst that exists in a different phase than the reactants (e.g., a solid metal catalyst and gas phase reactants), and the catalytic reaction generally occurs on the surface of the heterogeneous catalyst. Thus, for the catalytic reaction to occur, the reactants must diffuse to and/or adsorb onto the catalyst surface.

As used herein, "homogenous catalyst" refers to a catalyst that exists in the same phase as the reactants (e.g., a soluble organometallic catalyst and solvent-dissolved reactants).

Additional definitions may be provided herein.

II. Catalysts

The presently disclosed methods are directed to a heterogeneous class of bifunctional, copper-based catalysts.

The bifunctional catalysts comprise a support and copper metal. In certain embodiments, the catalyst support comprises a material selected from the group consisting of silica ($SiO_2$), carbon, alumina ($Al_2O_3$), and a combination thereof. In certain embodiments, the support is silica. In certain embodiments, the support comprises an "aluminosilicate," which is referred to herein as a support comprising a mixture of silica and alumina.

In certain embodiments, the catalyst support comprises a material selected from the group consisting of zeolite X, zeolite Y, zeolite A, faujasite, mordenite, ferrierite, PERLKAT 79-3, PERLKAT 29-3, PERLKAT 46-10, and mixtures thereof.

In certain embodiments, the catalyst support is ZSM-5, which is an aluminosilicate zeolite with the general chemical formula $(HAlO_2)_x(SiO_2)_y$. ZSM-5 is commercially available from Zeolyst. It is a medium pore zeolite with channels defined by ten-membered rings. In certain embodiments, the ratio of silica to alumina in HZSM-5 is from about 5 to about 150. In certain embodiments, the ratio of silica to alumina in HZSM-5 is from about 15 to about 100, or about 50 to about 75. In certain embodiments, the ratio of silica to alumina in HZSM-5 is about 15, about 40, or about 140.

In certain embodiments, the catalyst support is High Silica Zeolite Y, which is referred to herein as Zeolite Y. Zeolite Y is an aluminosilicate with a faujasite-type structure having large pores. Zeolite Y is commercially available from Zeolyst. In certain embodiments, the ratio of silica to alumina in Zeolite Y is from 2 to 25 or about 5 to 15. In certain embodiments, the ratio of silica to alumina in Zeolite Y is about 2.55. In certain embodiments, the ratio of silica to alumina in Zeolite Y is about 15.

In certain embodiments, the catalyst support is a silica, a commercial example of which is PERLKAT (BASF). The silica adsorbent may be selected from fused quartz, crystal silica, fumed silica, colloidal silica, silica gel, aerogel, transition metal substituted silica, alumina substituted silica, high purity silica, and mixtures thereof. In certain embodiments, the support is selected from the group consisting of PERLKAT 79-3, PERLKAT 29-3, and PERLKAT 46-10. In certain embodiments, the support is PERLKAT 79-3 or PERLKAT 46-10. In certain embodiments, PERLKAT 79-3 comprises alumina and silica. In certain embodiments, PERLKAT 79-3 contains about 4.05 wt % $Al_2O_3$. In certain embodiments, PERLKAT 29-3 contains about 1.94 wt % $Al_2O_3$. In certain embodiments, PERLKAT 46-10 contains about 2.50 wt % $Al_2O_3$.

In certain embodiments, the amount of copper loading in the catalyst is about 2 to about 30%. In certain embodiments, the amount of copper loading is about 5%, about 10%, or about 20%.

In certain embodiments, the bifunctional copper-based catalyst is selected from the group consisting of 10% $Cu/SiO_2$, 10% Cu/PERLKAT 46-10, 10% Cu/PERLKAT 79-3, 10% Cu/HZSM5, and 10% Cu/zeolite Y.

III. Furanic Ketones

The subject matter described herein is directed to a process for selectively hydrodeoxygenating a furanic ketone to an alkyl furan. The furanic ketone is a compound of Formula II

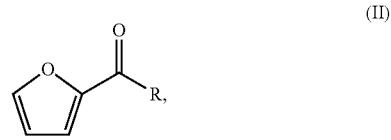

wherein R is alkyl.

In certain embodiments, R is linear or branched $C_{1-50}$ alkyl, linear or branched $C_{1-25}$ alkyl, or linear or branched $C_{1-20}$ alkyl.

In certain embodiments, R is a linear $C_{11}$ alkyl, wherein the compound of formula II has the following structure:

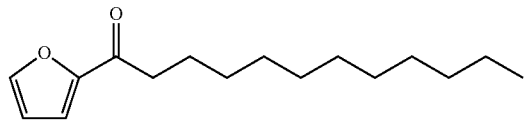

In certain embodiments, R is branched $C_7$ alkyl, wherein the compound of formula II has the following structure:

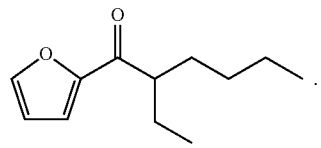

IV. General Methods

Disclosed herein is a method for preparing a compound of Formula I,

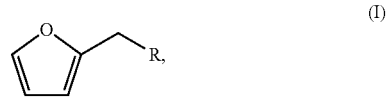

comprising contacting a compound of Formula II,

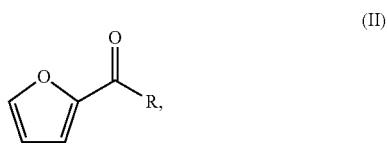

with a bifunctional copper-based catalyst for selective hydrodeoxygenation of the ketone moiety in the presence of a solvent, wherein R is alkyl.

In certain embodiments, said bifunctional copper-based catalyst is a heterogeneous catalyst selected from the group consisting of 10% Cu/zeolite Y, 10% Cu/HZSM-5, and 10% Cu-PERLKAT 79-3. In certain embodiments, the catalyst is 10% Cu/zeolite Y having a Si/Al ratio of 2.55. In certain embodiments, the catalyst is 5% Cu/Y (Si/Al=2.55). In certain embodiments the catalyst is 20% Cu/Y (Si/Al=2.55).

In certain embodiments, the solvent is selected from the group consisting of dimethylformamide (N,N-dimethylformamide) (DMF), dimethyl sulfoxide (DMSO), pyridine, dioxane, dichloromethane, perfluorohexane, α,α,α-trifluorotoluene, pentane, hexane, cyclohexane, methylcyclohexane, decalin, carbon tetrachloride, freon-11, benzene, dicholoromethane, toluene, triethyl amine, carbon disulfide, isopropyl acetate, diisopropyl ether, diethyl ether (ether), t-butyl methyl ether, chloroform, ethyl acetate, 1,2-dimethoxyethane (glyme), 2-methoxyethyl ether (diglyme), tetrahydrofuran (THF), methylene chloride, 2-butanone, acetone, hexamethylphosphoramide, N-methylpyrrolidinone, nitromethane, acetonitrile, sulfolane, and propylene carbonate. In certain embodiments, the solvent is selected from the group consisting of hexane, cyclohexane, dimethylformamide (DMF), dimethyl sulfoxide (DMSO), dichloromethane, pentane, tetrahydrofuran (THF), and acetone. In certain embodiments, the solvent is hexane.

In certain embodiments, the compound of Formula II is present in an amount of about 2 to about 15 moles or about 5 to about 10 moles relative to 1 mole of the bifunctional copper-based catalyst. In certain embodiments, the compound of Formula II is present in an amount of about 3 moles, 4 moles, 5 moles, 6 moles, 7 moles, 8 moles, 9 moles, 10 moles, 11 moles, or 12 moles relative to 1 mole of the bifunctional copper-based catalyst.

In certain embodiments, the compound of Formula II is present in a weight ratio of about 1 to 7 or about 2 to 4 relative to the bifunctional copper-based catalyst. In certain embodiments, the weight ratio of the compound of Formula II to the bifunctional copper-based catalyst is about 1:1, about 1:2, about 1:3, 1:4, 1:5, or about 1:6.

In certain embodiments, the method is performed at a temperature in a range of about 50° C. to about 300° C., about 100° C. to about 270° C., or about 160° C. to about 240° C. In certain embodiments, the method is performed at a temperature of about 160° C., 180° C., 200° C., 220° C., or about 240° C. The method can be carried out in a batch reactor or continuous flow reactor at any of the beforementioned temperatures or temperature ranges.

In certain embodiments, the method achieves at least 30%, 40%, 50%, 60%, 70%, 75%, 80%, 85%, 90%, 91%, 92%, 93%, 94%, 95%, 96%, 97%, 98%, 99%, or 100% selective hydrodeoxygenation of the ketone moiety.

In certain embodiments, the method achieves at least 30%, 40%, 50%, 60%, 70%, 75%, 80%, 85%, 90%, 91%, 92%, 93%, 94%, 95%, 96%, 97%, 98%, 99%, or 100% yield.

In certain embodiments, R is linear or branched $C_{1-50}$ alkyl, linear or branched $C_{1-25}$ alkyl, or linear or branched $C_{1-20}$ alkyl.

In certain embodiments, R is $C_{11}$ and the compound of Formula I is 2-n-dodecylfuran, having the following structure:

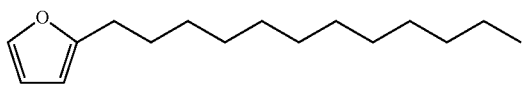 [SMILES: CCCCCCCCCCCCc1ccco1]

In certain embodiments, R is $C_7$ and the compound of Formula I is 2-(2-ethylhexyl)-furan, having the following structure:

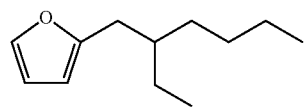

In certain embodiments, the method is carried out in a batch reactor. In certain embodiments, wherein the method is carried out in a batch reactor, the method is carried out in the presence of a hydrogen gas atmosphere. In certain embodiments, the method is carried out at an initial hydrogen gas pressure of about 50 to about 300 psi. In certain embodiments, the initial hydrogen pressure is about 100 psi, about 125 psi, about 150 psi, about 175 psi, or about 200 psi. In certain embodiments, wherein the method is carried out in a batch reactor, the method is carried out for about 2 to about 50 hours, for about 3 to about 25 hours, or from about 5 to about 15 hours. In certain embodiments, the method is carried out for about 3 hours, 4 hours, 5 hours, 6 hours, or 7 hours.

In certain embodiments, the method is carried out in a continuous flow reactor. In certain embodiments, wherein the method is carried out in a continuous flow reactor, the method is carried out in the presence of a flowing gas. In certain embodiments, the flowing gas is flowing hydrogen gas. In certain embodiments, the method is carried out in the presence of flowing hydrogen/argon gas. In certain embodiments, the flowing hydrogen/argon gas comprises a mixture of 50% hydrogen and 50% argon. In certain embodiments, the flowing hydrogen/argon gas comprises hydrogen/argon is a ratio of about 10:90, 20:80, 30:70, 40:60, 50:50, 60:40, 70:30, 80:20, or 90:10.

In certain embodiments, wherein the method is carried out in a continuous flow reactor, the flowing gas has a flow rate of about 5 mL/min to about 50 mL/min, about 10 mL/min to about 30 mL/min, or about 15 mL/min to about 25 mL/min. In certain embodiments, the flowing gas has a flow rate of about 18 mL/min, 19 mL/min, 20 mL/min, 21 mL/min, or 22 mL/min.

In certain embodiments, wherein the method is carried out in a continuous flow reactor, the compound of Formula II has a flow rate of about 0.05 to about 30 mL/min. In certain embodiments, the compound of Formula II has a flow rate of about 0.1 to about 10 mL/min or about 0.12 to about 3 mL/min. In certain embodiments, the compound of Formula II has a flow rate of about 0.13 mL/min, 0.14 mL/min, 0.15 mL/min, 0.16 mL/min, 0.17 mL/min, 0.18 mL/min, 0.19 mL/min, 0.2 mL/min, 0.21 mL/min, 0.25 mL/min, 0.30 mL/min, 0.40 mL/min, 0.60 mL/min, 0.80 mL/min, 1.0 mL/min, 1.5 mL/min, 2.0 mL/min, 2.8 mL/min, 3.7 mL/min, 5.0 mL/min, or 7.0 mL/min.

In certain embodiments, wherein the method is carried out in a continuous flow reactor, the method is carried out with a back pressure of about 1 psi to about 350 psi, about 5 psi to about 300 psi, about 75 psi to about 200 psi, about 90 psi to about 150 psi, or about 100 psi to about 125 psi. In certain embodiments, the method is carried out with a back pressure of about 50 psi, 95 psi, 96 psi, 99 psi, 100 psi, 102 psi, 105 psi, 110 psi, 120 psi, 125 psi, 135 psi, 145 psi, 150 psi, 175 psi, 200 psi, 225 psi, 250 psi, or 300 psi.

In certain embodiments, wherein the method is carried out in a continuous flow reactor, the method is carried out with a space time of about 1 to about 50 minutes, 2 to about 40 minutes, or 5 to about 30 minutes. In certain embodiments, the method is carried out with a space time of about 4 minutes, 5 minutes, 6 minutes, 8 minutes, 9 minutes, 10 minutes, 11 minutes, 15 minutes, 17 minutes, 18 minutes, 19 minutes, 20 minutes, 21 minutes, 22 minutes, 25 minutes, 27 minutes, 28 minutes, 29 minutes, 30 minutes, 31 minutes, or 32 minutes.

In certain embodiments, wherein the method is carried out in a continuous flow reactor, the method is carried out with a concentration stream of a compound of formula II of about 10 g/L to about 125 g/L, or about 25 g/L to about 100 g/L. In certain embodiments, the method is carried out with a concentration stream of a compound of formula II of about 10 g/L, about 15 g/L, about 25 g/L, about 35 g/L, about 50 g/L, about 75 g/L, or about 100 g/L.

In the method disclosed herein, said bifunctional copper-based catalyst is not copper chromite ($2CuO—Cr_2O_3$).

V. Schemes

In an aspect, the subject matter described herein is directed to processes for preparing a compound of Formula I in high yield with high purity from a compound of Formula II. Scheme 1-1 depicts an overview for such a synthesis.

Scheme 1-1

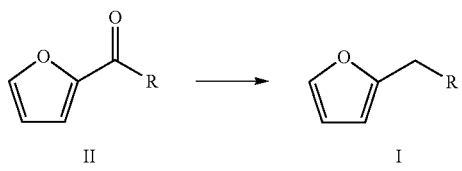

In certain embodiments, the methods described herein are directed to preparing 2-n-dodecylfuran in high yield with high purity from 1-(furan-2-yl)dodecan-1-one. Scheme 1-2 depicts an overview for such a synthesis.

Scheme 1-2

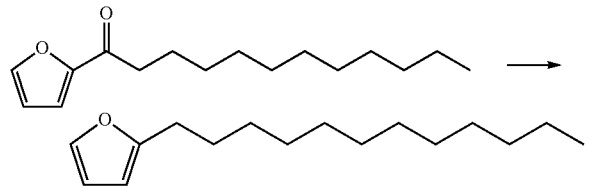

In certain embodiments, the methods described herein are directed to preparing 2-(2-ethylhexyl)-furan in high yield, with high purity, from 2-ethyl-1-(furan-2-yl)hexan-1-one. Scheme 1-3 depicts an exemplary route for such a synthesis.

Scheme 1-3

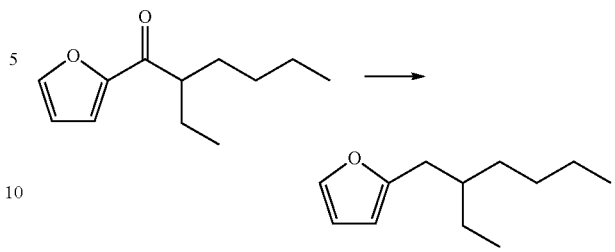

The subject matter described herein includes the following embodiments:

1. A method for preparing a compound of Formula I,

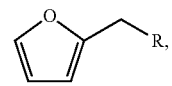

comprising contacting a compound of Formula II, (II)

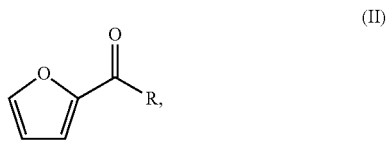

with a bifunctional copper-based catalyst for selective hydrodeoxygenation of the ketone moiety in the presence of a solvent,
wherein R is an alkyl.

2. The method of embodiment 1, wherein said bifunctional copper-based catalyst is a heterogeneous catalyst selected from the group consisting of 10% $Cu/SiO_2$, 10% Cu/PERLKAT 46-10, 10% Cu/PERLKAT 79-3, 10% Cu/HZSM5, and 10% Cu/zeolite Y.

3. The method of embodiment 1 or 2, wherein said bifunctional copper-based catalyst is a heterogeneous catalyst selected from the group consisting of 10% Cu/zeolite Y, 10% Cu/HZSM-5, and 10% Cu/PERLKAT 79-3.

4. The method of any one of embodiments 1-3, wherein the compound of Formula II is present in an amount of about 5 to about 10 moles relative to 1 mole of the bifunctional copper-based catalyst.

5. The method of any one of embodiments 1-4, wherein said solvent is selected from the group consisting of hexane, cyclohexane, dimethylformamide (DMF), dimethyl sulfoxide (DMSO), dichloromethane, pentane, tetrahydrofuran (THF), and acetone.

6. The method of any one of embodiments 1-5, wherein the solvent is hexane.

7. The method of any one of embodiments 1-6, wherein the method is performed at a temperature in the range of about 160° C. to about 240° C.

8. The method of any one of embodiments 1-7, wherein the method is performed at a temperature of about 220° C.

9. The method of any one of embodiment 1, wherein said alkyl is linear or branched $C_{1-20}$ alkyl.

10. The method of any one of embodiments 1-9, wherein said compound of Formula I is

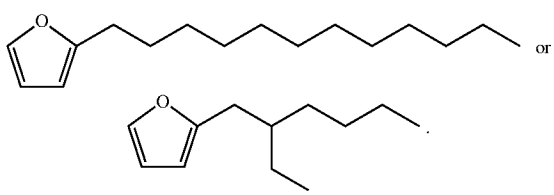

11. The method of any one of embodiments 1-10, wherein said alkyl is linear $C_{11}$ alkyl.

12. The method of any one of embodiments 1-11, wherein the method achieves at least 75% selective hydrodeoxygenation of the ketone moiety.

13. The method of any one of embodiments 1-11, wherein the method achieves at least 95% selective hydrodeoxygenation of the ketone moiety.

14. The method of any one of embodiments 1-11, wherein the method achieves at least 98% selective hydrodeoxygenation of the ketone moiety.

15. The method of embodiment 1, wherein the compound of Formula I is a compound for use in the preparation of a surfactant.

16. The method of any one of embodiments 1-15, wherein the method is carried out in a batch reactor.

17. The method of embodiment 16, wherein said reactor further comprises hydrogen gas.

18. The method of embodiment 17, wherein the method is carried out at an initial hydrogen gas pressure of about 50 to about 300 psi.

19. The method of embodiment 18, wherein said initial hydrogen pressure is about 150 psi.

20. The method of any one of embodiments 16-19, wherein the method is carried out for about 5 to about 15 hours.

21. The method of any one of embodiments 16-20, wherein the method is carried out for about 5 hours.

22. The method of any one of embodiments 1-15, wherein the method is carried out in a continuous flow reactor.

23. The method of embodiment 22, wherein said reactor further comprises flowing hydrogen/argon gas.

24. The method of embodiment 23, wherein the flowing hydrogen/argon gas comprises a mixture of 50% hydrogen and 50% argon.

25. The method of embodiment 23 or 24, wherein said flowing hydrogen/argon gas has a flow rate of about 20 mL/min.

26. The method of any one of embodiments 22-25, wherein said method is carried out with a back pressure of about 50 to about 300 psi.

27. The method of any one of embodiments 22-26, wherein said method is carried out with a back pressure of about 50 psi.

28. The method of any one of embodiments 22-27, wherein said method is carried out with a concentration stream of a compound of Formula II of about 25 g/L to about 100 g/L.

29. The method of any one of embodiments 1-28, wherein said bifunctional copper-based catalyst is not copper chromite ($2CuO-Cr_2O_3$).

The present invention is further described in the following non-limiting Examples. It should be understood that these Examples, while indicating preferred embodiments of the invention, are given by way of illustration only.

EXAMPLES

Materials

All of the chemicals and reagent grade solvents were obtained from commercial vendors and were used as received. $2CuO.Cr_2O_3$, $CuO/Al_2O_3$(13 wt %), $Cu(NO_3)_2.2.5H_2O$, $Ni(NO_3)_2.6H_2O$, $Co(NO_3)_2.6H_2O$, $CDCl_3$ (≥99.8%) and hexane (isomers mixtures, ≥98.5%) were obtained from Sigma Aldrich, and were used without any pretreatment. $SiO_2$ was obtained from Alfa Aesar, PERLKAT 46-10 and PERLKAT 79-3 were obtained from BASF, HZSM5 (Si/Al=15, 40, 140) and HSY (Si/Al=2.55, 15) were obtained from Zeolyst. All catalyst supports were dried and calcined under 550° C. for 4 hours with a ramp rate of 2° C./min in air flow before usage.

Characterization Methods

For the determination of Brunauer-Emmett-Teller (BET) surface areas, $N_2$ adsorption/desorption experiments were conducted at −196° C. (liquid $N_2$), using a Chembet-3000 Chemisorption analyzer after drying the samples at 110° C. under nitrogen flow for 10 hours. Multipoint surface area was determined using a Micromeritics ASAP 2020 surface area/porosity analyzer. Nitrogen was used as the adsorbate gas and the surface area was calculated using the BET gas adsorption method ($LN_2$ temperature). Samples were placed in glass sample cells and outgassed at 110° C. under vacuum for 6 hours prior to analysis.

Metal dispersion was carried out by using a Micromeritics chemisorption analyzer II 2920. Samples were pre-treated under hydrogen atmosphere (10% $H_2$/Ar gas) with a temperature ramp of 10° C./min from 25° C. to 350° C. and then held at 350° C. for 2 hours. Cooling to room temperature was performed under a helium atmosphere and CO pulse chemisorption was carried out at 25° C. Samples were analyzed three times and averaged.

Temperature-programmed desorption (TPD) of adsorbed $NH_3$ on catalysts was carried out using a Micromeritics AutoChem II 2920 Chemisorption Analyzer. Each experiment was initiated by pre-treating the catalyst sample in helium flowing at 50 cm³/min for 2 h at 500° C. The sample was then cooled to the desired adsorption temperatures, 25° C. $NH_3$ was adsorbed on the catalysts by flowing 10% $NH_3$ blended in helium stream for a total time of 60 min. The sample was then cooled to room temperature and flushed with helium for 60 min. Temperature-programmed desorption was carried out in flowing He (50 cm³/min) with a heating rate of 10° C./min from ambient temperature to 500° C.

GC-MS analysis was carried out using a Hewlett-Packard 6890 GC system equipped with a Hewlett-Packard 5973 mass selective detector, a Polyarc and an FID detector.

$^1H$ and $^{13}C$ NMR spectra were obtained at room temperature on a Bruker AV400 MHz spectrometer, with chemical shifts (δ) referenced to $CDCl_3$ signal ($^1H$ and $^{13}C$).

The conversion and selectivity data were obtained using the following equations:

$$\text{Conversion \%} = \left(1 - \frac{\text{moles of carbon in furanic ketone left after reaction}}{\text{moles of carbon in feeded furanic ketone}}\right) \times 100\%$$

$$\text{Yield \%} = \frac{\text{moles of carbon in desired alkyl furan produced}}{\text{moles of carbon in feeded furanic ketone}} \times 100\%$$

$$\text{Selectivity \%} = \frac{\text{Yield \%}}{\text{Conversion \%}} \times 100\%$$

Example 1

Procedure for Catalyst Synthesis-10% Cu/SiO₂, 10% Cu/PERLKAT 46-10, 10% Cu/PERLKAT 79-3, 10% Cu/HZSM5, 10% Cu/High Silica Zeolite Y (HSY)

All catalyst supports (SiO$_2$, PERLKAT 46-10, PERLKAT 79-3, HZSM5, HSY) were obtained as pellets, and were grinded and sieved to a standard particle diameter range (180-425 μm, Dp=326 μm). All catalysts were prepared by incipient wetness impregnation, using a desired amount of copper nitrate hexahydrate as a precursor. The precursor was dissolved in a certain amount of deionized water to form a precursor solution and added dropwise onto the processed support while manually strung to obtain catalysts of the desired metal loading (in most cases 10 wt %, unless otherwise stated). The catalysts were dried at 110° C. overnight and then calcined at 450° C. for 4 hours with a ramp rate of 2° C./min in air flow of 40 mL/min.

Example 2

Selective Hydrodeoxygenation (HDO) of 2-dodecanoylfuran in Batch Reactor

Scheme 1. Reaction pathway of selective hydrodeoxygenation (HDO) of furanic ketone (eg. 2-dodecanoylfuran) to alkyl furans (2-dodecylfuran). R$_1$ is C$_{11}$H$_{23}$.

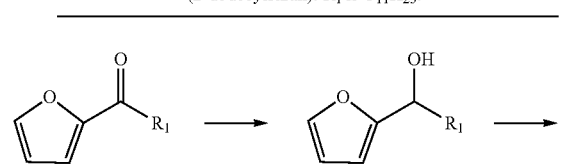

Figure 1B:
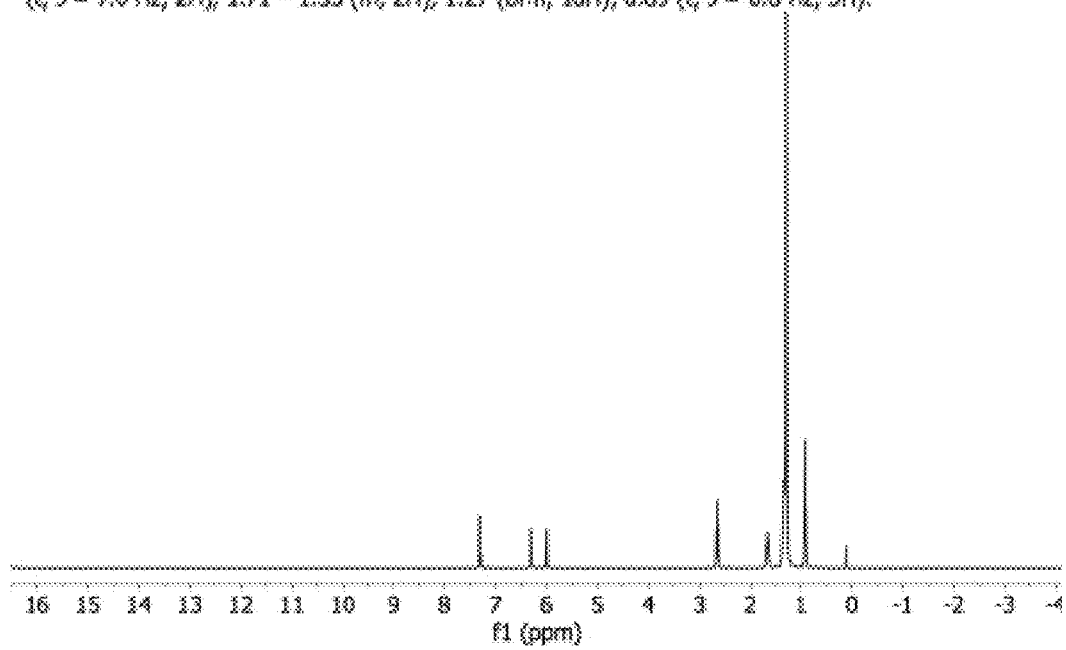
FIG. 1B shows NMR spectra of products from selective HDO of 2-dodecanoylfuran in a batch reaction. Reaction conditions: 0.1 g 2-dodecanoylfuran, 0.05 g 10% Cu/zeolite Y (Si/Al=2.55), 3 mL hexane, 220° C., $H_2$ atmosphere, 150 psi initial hydrogen pressure, 5 hours. The top spectrum depicts the $^1H$ NMR spectrum and the bottom spectrum depicts the $^{13}C$ NMR spectrum.
Figure 1B:
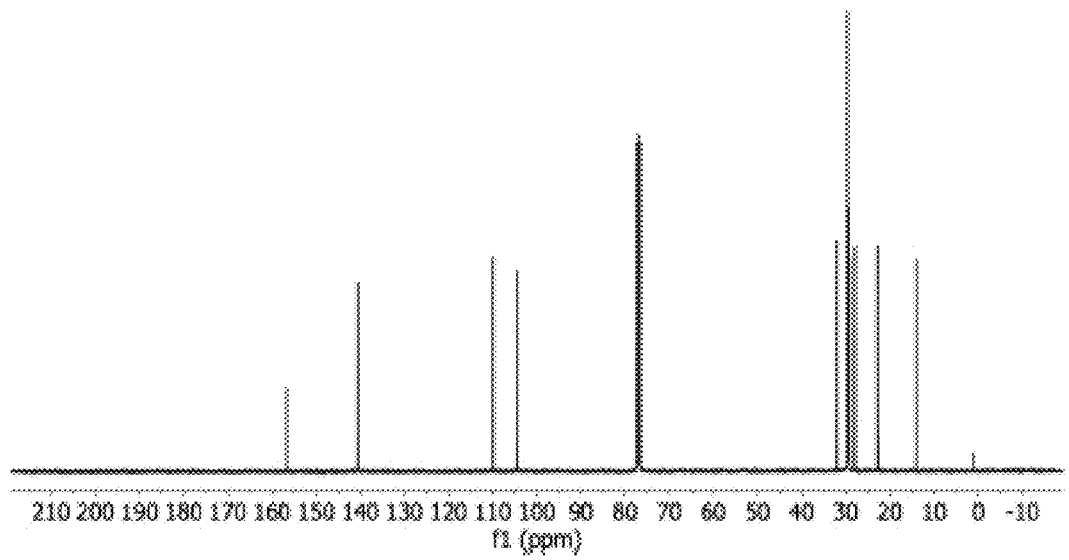

All reactions were carried out in a 50 mL stainless steel tube reactor containing a Teflon-lined stir bar. In a typical run, 2-dodecanoylfuran (0.10 g; 0.4 mmol) and solid catalyst (0.05 g) were added into the reactor, followed by hexanes (3 mL). The reactor was then sealed, purged with hydrogen gas and then charged with hydrogen gases to 150 psi. The reactor was heated to 220° C. and stirred at 500 rpm. After 5 hours, the tube was cooled to room temperature and vented, and the liquid products was collected and analyzed by GC-MS. GC results from selective HDO of 2-dodecanoylfuran in a batch reaction are provided in FIG. 1A. NMR results from selective HDO of 2-dodecanoylfuran in a batch reaction are provided in FIG. 1B.

Example 3

Catalyst Screening in Batch Reactor

Each catalyst was used directly without pre-treatment. Table 1 shows the catalyst screening entries, and summarizes a comparison of the conversion and selectivity data for different reaction catalysts. It can be seen that Cu/HSY (Si/Al=2.55) (Entry 2) exhibited higher selectivity than 2CuO—Cr$_2$O$_3$ (Entry 14) for selective HDO in batch reactions.

TABLE 1

Initial catalysts screening of 2-dodecanoylfuran selective HDO.

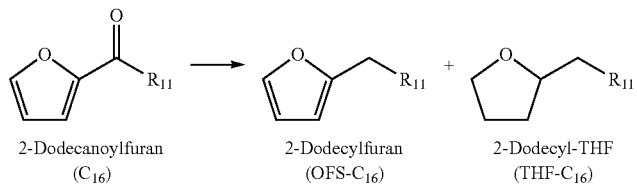

2-Dodecanoylfuran (C$_{16}$)   2-Dodecylfuran (OFS-C$_{16}$)   2-Dodecyl-THF (THF-C$_{16}$)

| Entry | Catalyst | Conversion, % | OFS-C$_{16}$ | THF-C$_{16}$ | Other by-products |
|---|---|---|---|---|---|
| 1 | None | 5.2 | 0 | 0 | 5.2 |
| 2 | 2CuO-Cr$_2$O$_3$ | 100 | 88.6 | 9.1 | 2.2 |
| 3 | CuO/Al$_2$O$_3$ | 85.6 | 60.5 | 8.3 | 16.7 |
| 4 | 10% Cu/SiO$_2$ | 96.2 | 74.2 | 0 | 22.0 |
| 5 | Cu(NO$_3$)$_2$ | 53.8 | 0 | 0 | 53.8 |
| 6 | ZSM5 (Si/Al = 15) | 0 | 0 | 0 | 0 |
| 7 | 10% Cu/P79-3 | 100 | 20.5 | 0 | 79.5 |
| 8 | 10% Cu/ZSM5 (Si/Al = 15) | 100 | 82.5 | 0 | 17.5 |
| 9 | 10% Ni/ZSM5 (Si/Al = 15) | 7.9 | 0 | 0 | 7.9 |
| 10 | 10% Co/ZSM5 (Si/Al = 15) | 49.0 | 0 | 0 | 49.0 |
| 11 | 10% Cu/ZSM5 (Si/Al = 40) | 91.6 | 65.1 | 6.5 | 28.5 |
| 12 | 10% Cu/ZSM5 (Si/Al = 140) | 100 | 48.5 | 13.6 | 28.4 |
| 13 | 10% Cu/HSY (Si/Al = 15) | 100 | 22.3 | 0 | 77.7 |

TABLE 1-continued

Initial catalysts screening of 2-dodecanoylfuran selective HDO.

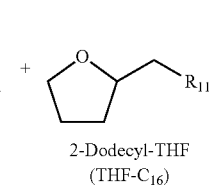

| | | | Yield, % | | |
|---|---|---|---|---|---|
| Entry | Catalyst | Conversion, % | OFS-$C_{16}$ | THF-$C_{16}$ | Other by-products |
| 14 | 10% Cu/HSY (Si/Al = 2.55) | 100 | 92.9 | 0 | 7.1 |
| 15 | 10% Cu/HSY (Si/Al = 2.55)[a] | 100 | >99 | 0 | 0 |

Reaction conditions: 0.1 g (0.4 mmol); feedstock was $C_{16}$ (2-dodecanoylfuran), catalyst 0.05 g, hexane 3 mL, initial pressure of hydrogen gas 150 psi, 220° C., 5 hours.
[a]Reaction time was longer than 8 hours.

Example 4

Continuous Reactor Experiments

Figure 2:
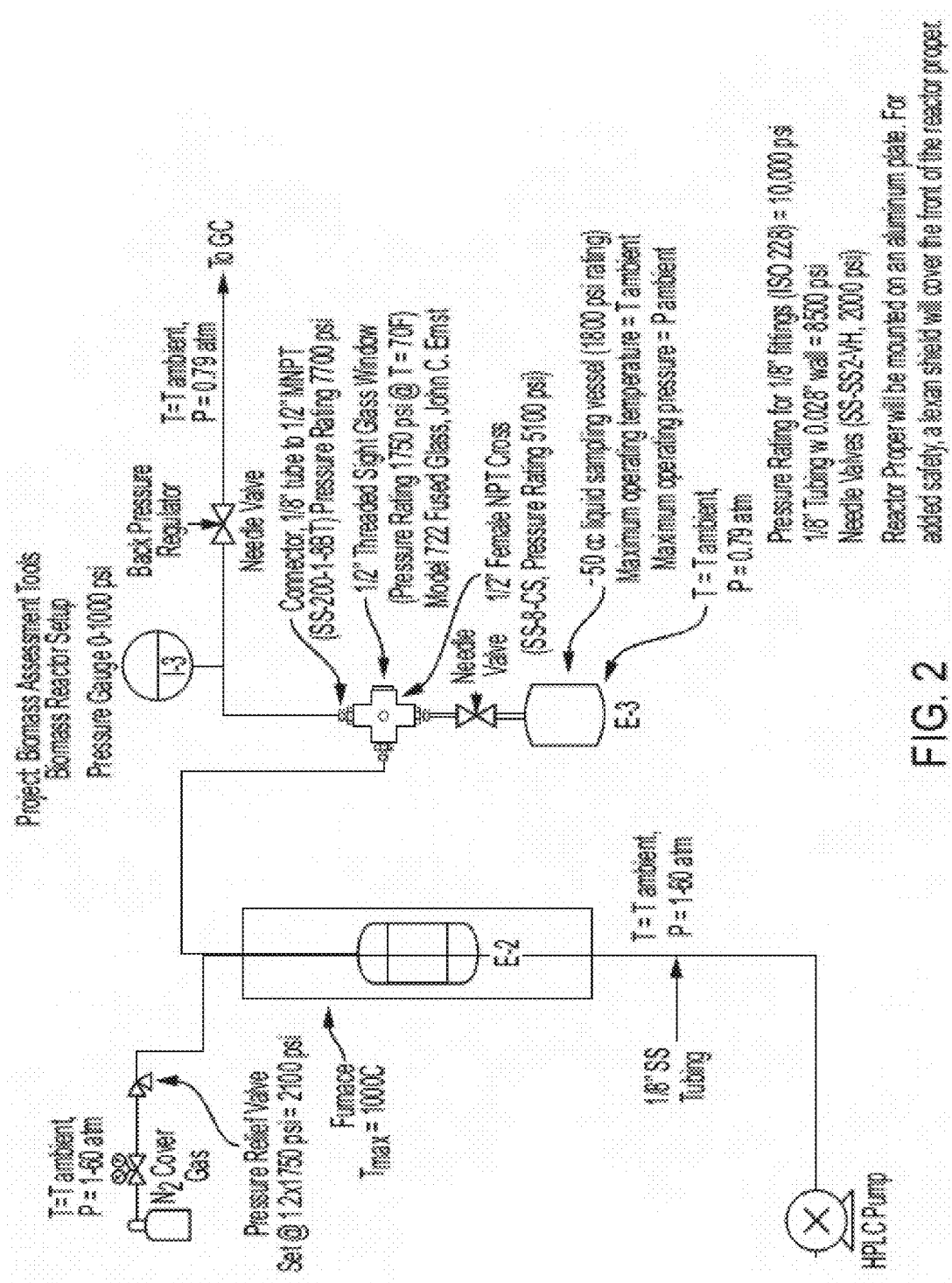
FIG. 2 shows a diagram of the continuous pack-bed reactor set-up.

Continuous 2-dodecanoylfuran selective hydrodeoxygenation studies were carried out in an isothermal packed-bed stainless steel reactor, with an internal diameter of 0.45 cm. The catalyst charges were kept in place with two 20 um stainless steel filters—one above and one below the catalyst charge. A diagram of the continuous pack-bed reactor set-up is provided in FIG. 2.

Example 5

Catalyst Screening Experiments in Continuous Flow Reactor

Cu based bi-functional catalysts were screened for their activity at a temperature of 220° C. with a space time of 10 min. Each experiment was carried out by flowing the reactant feed stream (50 g/L 2-dodecanoylfuran in hexanes) over the catalyst bed along with a flow of $H_2$ (20 mL/min, back pressure 100 psi) at the set temperature (220° C.). This was then allowed to reach steady state over 100 minutes, after which three samples of the product stream were taken in intervals of 10 minutes.

Figure 3A:
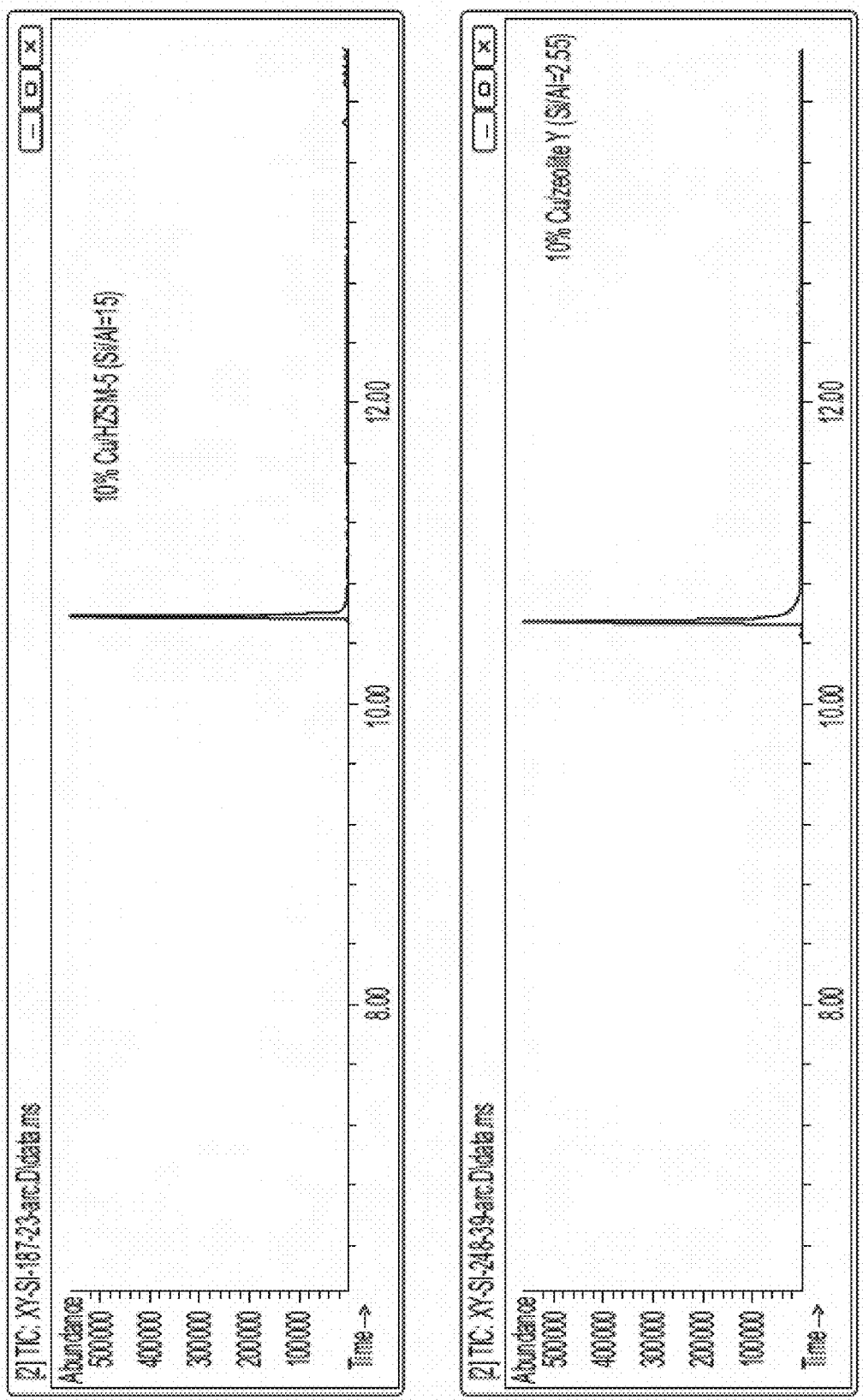
FIG. 3A shows GC-MS spectra of products from selective HDO of 2-dodecanoylfuran in a packed bed flow reactor. Top plot reaction conditions: 50 g/L 2-dodecanoylfuran in hexane, 0.155 mL/min flow rate, 1.0 g 10% Cu/HZSM-5 (Si/Al=15), 20 mL/min $H_2$/Ar (50%) flow rate, 100 psi back pressure, 220° C., 30 min space time. Bottom plot reaction conditions: 50 g/L 2-dodecanoylfuran in hexane, 0.155 mL/min flow rate, 1.0 g 10% Cu/zeolite Y (Si/Al=2.55), 20 mL/min $H_2$/Ar (50%) flow rate, 100 psi back pressure, 220° C., 30 min space time.
Figure 3B:
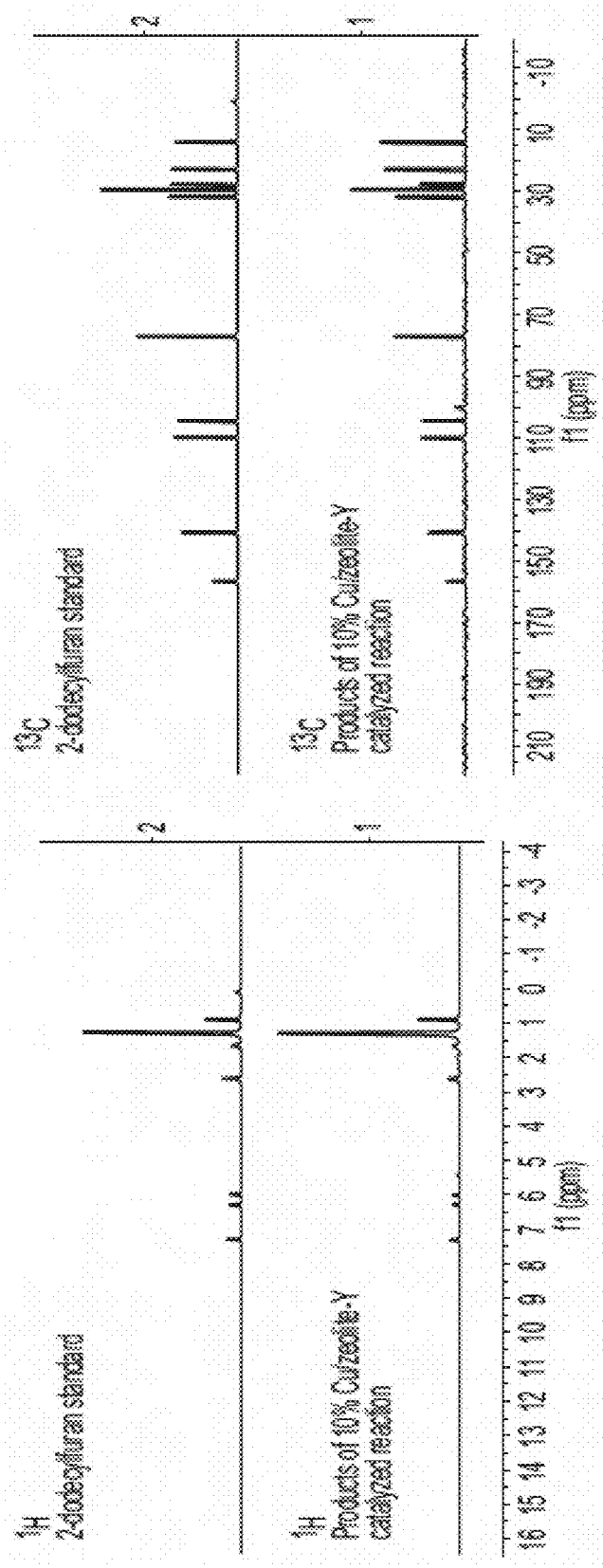
FIG. 3B shows NMR spectra of products from the selective HDO of 2-dodecanoylfuran in a packed bed flow reactor. Reaction conditions: 50 g/L 2-dodecanoylfuran in hexane, 0.155 mL/min flow rate, 1.0 g 10% Cu/zeolite Y (Si/Al=2.55), 20 mL/min $H_2$/Ar (50%) flow rate, 100 psi back pressure, 220° C., 30 min space time.

Both Cu/zeolite Y and Cu/HZSM-5 showed high conversion and selectivity in continuous flow reactions. The products distributions of 2-dodecanoylfuran conversions were characterized by GC-MS and NMR, as shown in FIG. 3A and FIG. 3B, respectively. Both results show 2-dodecylfuran was the major product with trace amount of by-products. Table 2 through Table 8 summarize the continuous flow reactor results.

TABLE 2

Catalyst screening & Si/Al ratio of solid acid support effect in continuous reactor.

| Catalyst | Conversion, % | Yield, % |
|---|---|---|
| 10% Cu/zeolite-Y (Si/Al = 2.55) | 100 | 97.8 |
| 10% Cu/zeolite-Y (Si/Al = 15) | 100 | 38.6 |
| 10% Cu/HZSM-5 (Si/Al = 15) | 99.3 | 93.4 |
| 10% Cu/HZSM-5 (Si/Al = 40) | 100 | 84.2 |
| 10% Cu/HZSM-5 (Si/Al = 140) | 100 | 66.2 |
| 10% Cu/PERLKAT 79-3 (Si/Al = 10) | 100 | 7.7 |

Reaction conditions: 50 g/L 2-dodecanoylfuran in hexane, flow rate 0.15 mL/min, catalyst 1.0 g, 50% $H_2$/Ar flow rate 20 mL/min, back pressure 100 psi, temperature 220° C., space time 10 mins.

TABLE 3

Temperature effect in continuous reactor.

| Temperature, ° C. | Conversion, % | Yield, % |
|---|---|---|
| 160 | 100 | 38.8 |
| 180 | 100 | 58.2 |
| 200 | 100 | 76.9 |
| 220 | 100 | 97.8 |
| 240 | 100 | >99.0 |

Reaction conditions: 50 g/L 2-dodecanoylfuran in hexane, flow rate 0.15 mL/min, 10% Cu/zeolite Y (Si/Al=2.55) 1.0 g, 50% $H_2$/Ar flow rate 20 mL/min, back pressure 100 psi, temperature 160-240° C., space time 10 mins.

TABLE 4

Space time effect in continuous reactor.

| Space time, mins | Conversion, % | Yield, % |
|---|---|---|
| 5 | 100 | 61.1 |
| 10 | 100 | 97.8 |
| 20 | 100 | 99.2 |
| 30 | 100 | >99.0 |

Reaction conditions: 50 g/L 2-dodecanoylfuran in hexane, flow rate 0.15 mL/min, 10% Cu/zeolite Y (Si/Al=2.55) 1.0 g, 50% $H_2$/Ar flow rate 20 mL/min, back pressure 100 psi, temperature 220° C., space time 5-30 mins.

TABLE 5

Metal loading effect in continuous reactor.

| Catalyst | Conversion, % | Yield, % |
| --- | --- | --- |
| 5% Cu/zeolite Y (Si/Al = 2.55) | 100 | 76.8 |
| 10% Cu/zeolite Y (Si/Al = 2.55) | 100 | 97.8 |
| 20% Cu/zeolite Y (Si/Al = 2.55) | 100 | 12.7 |

Reaction conditions: 50 g/L 2-dodecanoylfuran in hexane, flow rate 0.15 mL/min, catalyst 1.0 g, 50% $H_2$/Ar flow rate 20 mL/min, back pressure 100 psi, temperature 220° C., space time 10 mins.

TABLE 6

Back pressure effect in continuous reactor.

| Back pressure | Conversion, % | Yield, % |
| --- | --- | --- |
| 50 | 100 | >99.0 |
| 100 | 100 | 97.8 |
| 150 | 100 | 50.7 |
| 200 | 100 | 43.7 |
| 300 | 100 | 49.8 |

Reaction conditions: 50 g/L 2-dodecanoylfuran in hexane, flow rate 0.15 mL/min, 10% Cu/zeolite Y (Si/Al=2.55) 1.0 g, 50% $H_2$/Ar flow rate 20 mL/min, back pressure 50-300 psi, temperature 220° C., space time 10 mins.

TABLE 7

Hydrogen flow rate effect in continuous reactor.

| $H_2$ flow rate | Conversion, % | Yield, % |
| --- | --- | --- |
| 5 | 100 | 31.9 |
| 10 | 100 | 94.8 |
| 20 | 100 | 97.8 |
| 30 | 100 | 89.6 |

Reaction conditions: 50 g/L 2-dodecanoylfuran in hexane, flow rate 0.15 mL/min, 10% Cu/zeolite Y (Si/Al=2.55) 1.0 g, 50% Ar flow rate 5-30 mL/min, back pressure 100 psi, temperature 220° C., space time 10 mins.

TABLE 8

Concentration of feed stream effect in continuous reactor

| Concentration of feed stream, g/L | Conversion, % | Yield, % |
| --- | --- | --- |
| 25 | 100 | >99.0 |
| 50 | 100 | 97.8 |
| 100 | 100 | 46.6 |

Reaction conditions: 25-100 g/L 2-dodecanoylfuran in hexane, flow rate 0.15 mL/min, 10% Cu/zeolite Y (Si/Al=2.55) 1.0 g, 50% Ar flow rate 20 mL/min, back pressure 100 psi, temperature 220° C., space time 10 mins.

Example 6

Product Identification 2-n-dodecylfuran $^1$H NMR (400 MHz, Chloroform-d) δ 7.30 (dd, J=1.8, 1.1 Hz, 1H), 6.28 (dd, J=3.3, 1.8 Hz, 1H), 5.97 (dd, J=3.3, 1.1 Hz, 1H), 2.62 (t, J=7.6 Hz, 2H), 1.71-1.53 (m, 2H), 1.27 (brm, 18H), 0.89 (t, J=6.8 Hz, 3H).
$^{13}$C NMR (101 MHz, Chloroform-d) δ 156.65, 140.60, 110.01, 104.49, 31.94, 29.68, 29.66, 29.57, 29.39, 29.37, 29.21, 28.06, 28.00, 22.70, 14.12.
GCMS (EI) m/z (relative intensity): 236 (15.7), 137 (8.4), 123 (16.4), 96 (11.4), 95 (54.7), 94 (13.3), 82 (40.7), 81 (99.9), 55 (8.5), 53 (12.3)

2-(2-ethylhexyl)-furan $^1$H NMR (400 MHz, Chloroform-d) δ 7.30 (dd, J=1.8, 0.8 Hz, 1H), 6.28 (dd, J=3.1, 1.9 Hz, 1H), 5.98 (dd, J=3.1, 0.8 Hz, 1H), 2.57 (d, J=6.7 Hz, 2H), 1.64 (s, 1H), 1.31 (brm, J=28.5 Hz, 6H), 0.89 (brm, J=18.2 Hz, 8H).
$^{13}$C NMR (101 MHz, Chloroform-d) δ 155.63, 140.64, 110.00, 105.74, 38.70, 32.71, 32.00, 28.89, 25.90, 23.01, 14.12, 10.85.
GCMS (EI) m/z (relative intensity): 180 (32.8), 151 (6.7), 123 (9.3), 83 (8.1), 82 (99.9), 81 (80.5), 77 (5.5), 57 (60.6), 55 (7.6), 53 (18.6)

Example 7

Catalyst Time-On-Stream and Recycling

Figure 4:
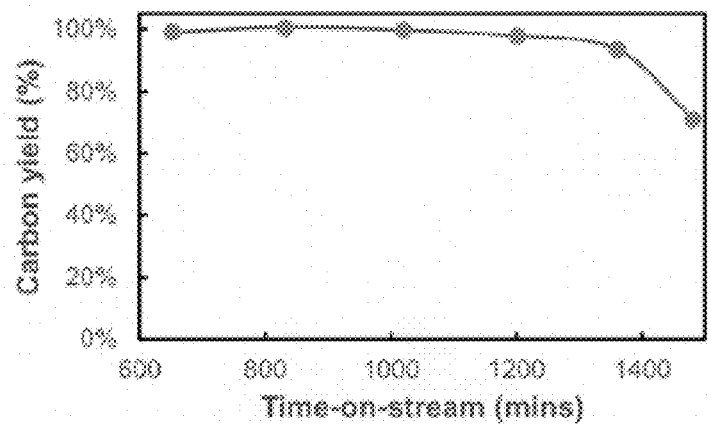
FIG. 4 shows the time-on-stream (28 hours) with 10% Cu/HSY (Si/Al=2.55) as the catalyst, space time=30 mins.

Catalysts were kept on stream for >24 hours under typical reaction conditions. FIG. 4 shows the time-on-stream with 10% Cu/HSY (Si/Al=2.55) as the catalyst with a space time of 30 mins. Reaction conditions: 50 g/L 2-dodecanoylfuran in hexane, flow rate 0.155 mL/min, 10% Cu/HSY (Si/Al=2.55) 1.0 g, 50% $H_2$/Ar flow rate 20 mL/min, back pressure 100 psi, temperature 220° C., space time 30 mins.

Figure 5:
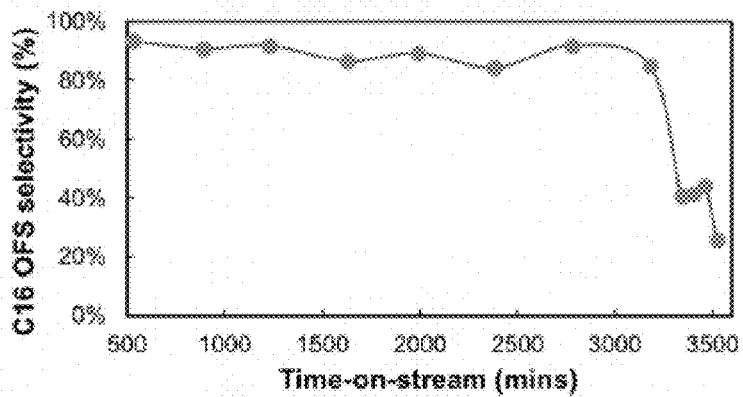
FIG. 5 shows the time-on-stream (56 hours) with 10% Cu/HSY (Si/Al=2.55) as the catalyst, space time=10 mins.

FIG. 5 shows the time-on-stream with 10% Cu/HSY (Si/Al=2.55) as the catalyst with a space time of 10 mins. Reaction conditions: 50 g/L 2-dodecanoylfuran in hexane, flow rate 0.155 mL/min, 10% Cu/HSY (Si/Al=2.55) 1.0 g, 50% $H_2$/Ar flow rate 20 mL/min, back pressure 100 psi, temperature 220° C., space time 10 mins. It was determined that a shorter space time would slightly decrease the product yield. However, an increased time-on-stream with high yield (~90%) was observed to last for 53 hours.

Figure 6:
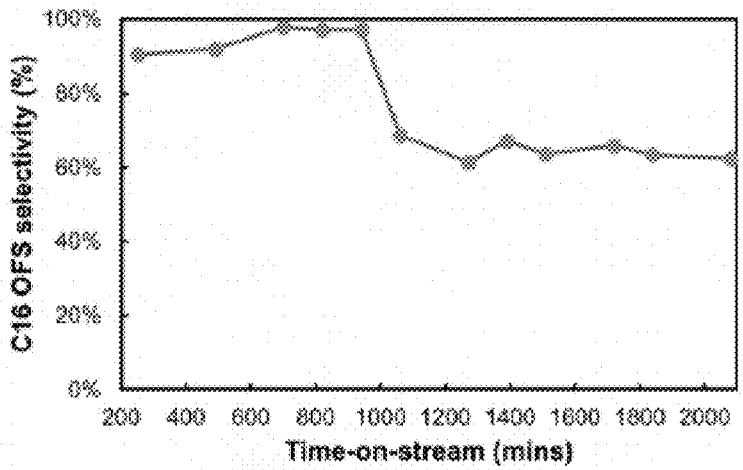
FIG. 6 shows the time-on-stream (34 hours) with 10% Cu/HZSM5 (Si/Al=15) as the catalyst, space time=10 mins.

FIG. 6 shows the time-on-stream with 10% Cu/HZSM5 (Si/Al=15) as the catalyst with a space time of 10 mins. Reaction conditions: 50 g/L 2-dodecanoylfuran in hexane, flow rate 0.155 mL/min, 10% Cu/HZSM5 (Si/Al=15) 1.0 g, 50% H₂/Ar flow rate 20 mL/min, back pressure 100 psi, temperature 220° C., space time 10 mins. It can be seen that the 10% Cu/HZSM5 (Si/Al=15) catalyst performed well (>95%) in 16 hours.

In the regeneration procedure, the used catalyst was collected, washed with acetone at room temperature, and dried in air overnight. Then, the dried used catalyst was further calcined in air flow at 450° C. for 6 hours. There was no further treatment before reuse. Table 9 summarizes the rerun reaction data obtained using a continuous reactor.

TABLE 9

Rerun reaction with regenerated catalyst in continuous reactor.

| Catalyst | Space time, min | Conversion, % | Yield, % |
|---|---|---|---|
| Regenerated 10% Cu/zeolite-Y (SAR = 2.55) | 10 | 100 | 48.4 |
| Regenerated 10% Cu/zeolite-Y (SAR = 2.55) | 20 | 100 | 66.1 |

Reaction conditions: 50 g/L 2-dodecanoylfuran in hexane, flow rate 0.15 mL/min, regenerated 10% Cu/zeolite-Y (SAR=2.55) 1.0 g, 50% H₂/Ar flow rate 20 mL/min, back pressure 100 psi, temperature 220° C., space time 10 mins.

Efforts have been made to ensure accuracy with respect to numbers used (e.g. amounts, temperature, etc.) but some experimental errors and deviations should be accounted for.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The disclosures of all cited references including publications, patents, and patent applications are expressly incorporated herein by reference in their entirety.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller ranges is also encompassed, subject to any specifically excluded limit in the stated range. Where the stated range includes one or both of the limits, ranges excluding either or both of those included limits are also included.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation. One skilled in the art will recognize many methods and materials similar or equivalent to those described herein, which could be used in the practicing the subject matter described herein. The present disclosure is in no way limited to just the methods and materials described.

What is claimed is:

1. A method for preparing a compound of Formula I,

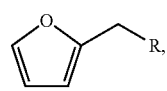
(I)

comprising contacting a compound of Formula II,

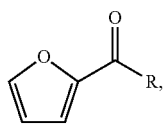
(II)

with a bifunctional copper-based catalyst for selective hydrodeoxygenation of the ketone moiety in the presence of a solvent,
wherein said bifunctional copper-based catalyst is a heterogeneous catalyst selected from the group consisting of 10% Cu/SiO₂, 10% Cu/PERLKAT 46-10, 10% Cu/PERLKAT 79-3, 10% Cu/HZSM5, and 10% Cu/zeolite Y,
wherein R is a linear or branched $C_{1-20}$ alkyl, and
wherein the method is carried out in a continuous flow reactor.

2. The method of claim 1, wherein said bifunctional copper-based catalyst is a heterogeneous catalyst selected from the group consisting of 10% Cu/zeolite Y, 10% Cu/HZSM-5, and 10% Cu/PERLKAT 79-3.

3. The method of claim 1, wherein the compound of Formula II is present in an amount of about 5 to about 10 moles relative to 1 mole of the bifunctional copper-based catalyst.

4. The method of claim 1, wherein said solvent is selected from the group consisting of hexane, cyclohexane, dimethylformamide (DMF), dimethyl sulfoxide (DMSO), dichloromethane, pentane, tetrahydrofuran (THF), and acetone.

5. The method of claim 4, wherein the solvent is hexane.

6. The method of claim 1, wherein the method is performed at a temperature in the range of about 160° C. to about 240° C.

7. The method of claim 6, wherein the method is performed at a temperature of about 220° C.

8. The method of claim 1, wherein said compound of Formula I is

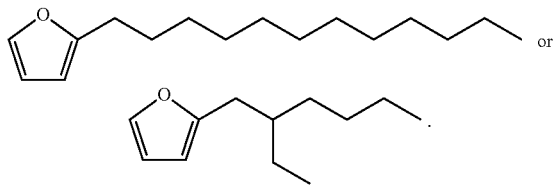 or

9. The method of claim 1, wherein said alkyl is linear $C_{11}$ alkyl.

10. The method of claim 1, wherein the method achieves at least 75% selective hydrodeoxygenation of the ketone moiety.

11. The method of claim 1, wherein the method achieves at least 95% selective hydrodeoxygenation of the ketone moiety.

12. The method of claim 1, wherein the method achieves at least 98% selective hydrodeoxygenation of the ketone moiety.

13. The method of claim 1, wherein the compound of Formula I is a compound for use in the preparation of a surfactant.

14. The method of claim 1, wherein said reactor further comprises flowing hydrogen/argon gas.

15. The method of claim 14, wherein the flowing hydrogen/argon gas comprises a mixture of 50% hydrogen and 50% argon.

16. The method of claim 15, wherein said flowing hydrogen/argon gas has a flow rate of about 20 mL/min.

* * * * *